United States Patent
Freudenberger

(10) Patent No.: US 9,949,705 B2
(45) Date of Patent: Apr. 24, 2018

(54) DEVICE AND METHOD FOR X-RAY PHASE CONTRAST IMAGING

(71) Applicant: Jörg Freudenberger, Kalchreuth (DE)

(72) Inventor: Jörg Freudenberger, Kalchreuth (DE)

(73) Assignee: Siemens Aktiengesellschaft, München (DE)

(*) Notice: Subject to any disclaimer, the term of this patent is extended or adjusted under 35 U.S.C. 154(b) by 167 days.

(21) Appl. No.: 14/919,926

(22) Filed: Oct. 22, 2015

(65) Prior Publication Data
US 2016/0113610 A1  Apr. 28, 2016

(30) Foreign Application Priority Data
Oct. 23, 2014 (DE) .................. 10 2014 221 599

(51) Int. Cl.
| | | |
|---|---|---|
| *G01N 23/04* | (2006.01) | |
| *A61B 6/00* | (2006.01) | |
| *A61B 6/04* | (2006.01) | |

(52) U.S. Cl.
CPC ............ *A61B 6/484* (2013.01); *A61B 6/0407* (2013.01); *A61B 6/0492* (2013.01); *A61B 6/4035* (2013.01); *A61B 6/4291* (2013.01); *A61B 6/5235* (2013.01)

(58) Field of Classification Search
CPC ..... A61B 6/484; A61B 6/4291; A61B 6/0407; A61B 6/0492; A61B 6/4035; A61B 6/5235
USPC ........................................ 378/36, 163, 204
See application file for complete search history.

(56) References Cited

U.S. PATENT DOCUMENTS

| 2007/0189456 A1* | 8/2007 | Haras ................... A61B 6/08 378/98.5 |
| 2010/0246764 A1* | 9/2010 | Itoh ....................... G21K 1/025 378/62 |
| 2012/0140884 A1* | 6/2012 | Iwakiri ................ A61B 6/4233 378/62 |

(Continued)

FOREIGN PATENT DOCUMENTS

| CN | 101036584 A | 9/2007 |
| CN | 102047344 A | 5/2011 |

(Continued)

OTHER PUBLICATIONS

Clinical boudary conditions for grating-based differential phase-contrast mammography Ewald Roessl, Heiner Daerr, Thomas Koehler, Gerhard Martens and Udo van de Stevendaal Philosophical Transactions of the Royal Society, 2014 Philips Technologie GmbH, Hamburg, Germany, 2014.

(Continued)

*Primary Examiner* — Courtney Thomas
(74) *Attorney, Agent, or Firm* — Lempia Summerfield Katz LLC

(57) ABSTRACT

A device for slot scanning phase contrast x-ray imaging, includes an x-ray emitter, a plurality of x-ray gratings, a patient couch, and an x-ray detector. Position marker elements are arranged and configured in the beam path of the x-ray emitter such that the position marker elements are visible in an x-ray image. In the x-ray image, a relative position of an object on the patient couch in relation to an x-ray beam fan of the x-ray emitter may be established from a location and a distance of the position marker elements from one another.

12 Claims, 2 Drawing Sheets

(56) References Cited

U.S. PATENT DOCUMENTS

2012/0163535 A1\* 6/2012 Kaneko .............. A61B 6/4291
378/62
2013/0259194 A1\* 10/2013 Yip ..................... A61B 6/502
378/37
2014/0185746 A1 7/2014 Baturin et al.

FOREIGN PATENT DOCUMENTS

| CN | 102525504 A | 7/2012 |
|----|-------------|--------|
| CN | 102590912 A | 7/2012 |
| DE | 102007023925 A1 | 11/2008 |
| DE | 102010017425 A1 | 12/2011 |
| DE | 102010039598 A1 | 2/2012 |
| DE | 102011083416 A1 | 3/2013 |
| EP | 1879020 A1 | 1/2008 |
| EP | 2509503 A1 | 10/2012 |
| EP | 1887936 B1 | 12/2013 |
| WO | WO2013111050 A1 | 8/2013 |

OTHER PUBLICATIONS

Development of New Imaging System Based on Grating Interferometry: Preclinical Study in Breast Imaging Tokiko Endo, Shu Ichihara, Suzuko Moritani, Mikinao Ooiwa, Misaki Shiraiwa, Takako Morita, Yasuyuki Sato, Junko Kiyohara and Sumiya Nagatsuka p. 488 to 493 Springer International Publishing Switzerland 2014.
German Office action for related German Application No. 10 2014 221 599.4, dated May 15, 2015, with English Translation.
Chinese Office Action for Chinese Patent Application No. 201510691690.4, dated Feb. 8, 2018.

\* cited by examiner

DEVICE AND METHOD FOR X-RAY PHASE CONTRAST IMAGING

CROSS-REFERENCE TO RELATED APPLICATIONS

The present patent document claims the benefit of DE 102014221599.4, filed on Oct. 23, 2014, which is hereby incorporated by reference in its entirety.

TECHNICAL FIELD

The present embodiments relate to a device and a method for slot scanning x-ray phase contrast imaging.

BACKGROUND

X-ray phase contrast imaging is an x-ray imaging method that, unlike conventional x-ray instruments, does not only use the absorption by an object as source of information. X-ray phase contrast imaging combines the absorption with the shift of the phase of the x-ray radiation when passing through the object. The information content is disproportionately higher because the absorption supplies accurate images of the strongly absorbing bones and the phase contrast makes sharp images of the structures of the soft tissue. This offers the possibility of being able to identify pathological changes, such as the emergence of tumors, vessel constrictions, or pathological changes of cartilage, substantially earlier than previously.

The passage of x-ray radiation through matter is described by a complex refractive index. The imaginary part of the refractive index specifies the strength of the absorption, whereas the real part of the refractive index specifies the phase shift of the x-ray wave passing through a material. During phase contrast imaging, the phase information of the local phase or of the local gradient of the phase of the wavefront passing through an object is determined. Analogously to x-ray tomography, it is also possible to reconstruct tomographic representations of the phase shift based on a multiplicity of images.

There are a number of options for realizing x-ray phase contrast imaging. Known solutions are directed to making the phase shift of the x-ray radiation visible as an intensity variation when passing through an object via special arrangements and methods. One method is grating phase contrast imaging, also referred to as Talbot-Lau interferometry (e.g., European Patent Application No. EP 1 879 020 A1). The essential part of the Talbot-Lau interferometer consists of three x-ray gratings arranged between an x-ray tube and an x-ray detector.

In addition to the conventional absorption image, such interferometers may depict two additional measurement parameters in the form of further images: the phase contrast image and the dark-field image. The phase of the x-ray wave is determined by interference with a reference wave by using the interferometric grating arrangement.

For example, European Patent Application No. EP 1 879 020 A1 discloses an arrangement including an x-ray tube and a pixelated x-ray detector, between which an object to be irradiated is arranged. A source grating, also referred to as a coherence grating, is arranged between the focal point of the x-ray tube and the object. The source grating serves to simulate a plurality of line sources with a spatial partial coherence of the x-ray radiation, a precondition for interferometric imaging.

A diffraction grating, also referred to as a phase grating or Talbot grating, is arranged between the object and the x-ray detector. The diffraction grating impresses a phase shift (e.g., typically pi) onto the phase of the wavefront.

An absorption grating between the diffraction grating and the x-ray detector serves for measuring the phase shift generated by the object. The wavefront upstream of the object is "bent" by the object. The three gratings are to be arranged parallel to one another and at exact distances from one another.

The x-ray detector serves for the spatially dependent detection of x-ray quanta. Because the pixelation of the x-ray detector is generally not sufficient to resolve the interference strips of the Talbot pattern, the intensity pattern is scanned by shifting one of the gratings (e.g., "phase stepping"). Scanning is performed step-by-step or continuously in a direction perpendicular to a direction of the x-ray beam and perpendicular to the slit direction of the absorption grating. Three different types of x-ray images, the absorption image, the phase contrast image, and the dark-field image, may be recorded or reconstructed.

As an alternative to "phase stepping," the "slot scanning method," where the table with the object is displaced relative to the x-ray emitter and the gratings, may be used. By way of example, PCT Application No. WO 2013/111050 A1 describes such a method. The gratings may also be selected to be smaller, or partial gratings arranged next to one another may be used. In order to put together the individual images required for the slot-scanning method, the position of the object is to be known exactly in relation to the beam fan of the x-ray emitter. The main components of the system are mechanically connected to one another and equipped with complicated measurement aids. With known arrangements, a measurement accuracy of 0.3 to 1.0 mm is achievable.

In the case of a stationary patient table and a stationary detector in the slot scanning method, a fan beam of the x-ray emitter may be moved relative to the patient table and detector. However, for phase contrast imaging, the three x-ray gratings are also to be displaced in the process. Therefore, this option is more complicated.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a device and a method for slot scanning x-ray phase contrast imaging, where a relative position between an object and an x-ray beam fan passing through the object may be established more accurately, are provided.

According to one or more of the present embodiments, a slot scanning phase contrast x-ray imaging device includes position marker elements on one of the x-ray gratings and on the patient couch. The position marker elements are configured and arranged such that the position marker elements are visible in an x-ray image. The locations of the position marker elements in relation to one another are used for establishing the relative position. Therefore, the position marker elements serve as adjustment aids. The relative position may be established from the x-ray image by image processing software.

In an embodiment, a device for slot scanning phase contrast x-ray imaging is provided. The device includes an x-ray emitter, a plurality of x-ray gratings, a patient couch, and an x-ray detector. Position marker elements are arranged in the beam path of the x-ray emitter. The position marker elements are provided such that the position marker elements are visible in an x-ray image, and a relative position of an object on the patient couch in relation to an x-ray beam fan of the x-ray emitter is establishable in the x-ray image from the location of the position marker elements and the distance from one another.

The disclosed embodiments may offer the advantage that a costly, exact mechanical adjustment of components of the device is made superfluous.

In one embodiment, the position marker elements include a first position marker element and a second position marker element.

In a further embodiment, the first position marker element may be arranged on one of the x-ray gratings, and the second position marker element may be arranged on the patient couch.

In a further embodiment, a plurality of second position marker elements may be arranged on the surface of a couch board of the patient couch in the longitudinal direction of the couch board.

An image processing unit may establish the location and the distance of the position marker elements from one another.

In an embodiment, the position marker elements may be provided as a cross, as a circular ring, or as a triangle.

In a further embodiment, the position marker elements may have regions that are visible in the dark-field image, in the phase contrast image, in the absorption image, or in any combination of these images.

In one embodiment, the position marker elements may have a layer thickness of 10 μm to 500 μm and a diameter of 150 μm to 25 mm.

One or more of the present embodiments also provide a method for slot scanning phase contrast x-ray imaging. With the aid of position marker elements that are visible in an x-ray image and arranged in the beam path of an x-ray emitter, a relative position of an object to be irradiated in relation to an x-ray beam fan of the x-ray emitter is established from the location and the distance of the position marker elements from one another in the x-ray image.

In an embodiment, the position marker elements may include a first position marker element and a second position marker element.

In a further embodiment, the first position marker element may be arranged on an x-ray grating, and the second position marker element may be arranged on a patient couch carrying the object.

Image processing software may be used to establish the location and the distance of the first position marker element from the second position marker element.

DETAILED DESCRIPTION

Figure 1:
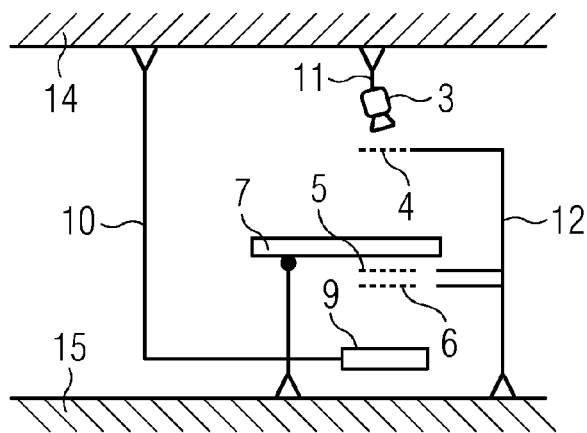
FIG. 1 depicts one embodiment of a slot scanning device with a floor and ceiling stand.
Figure 2:
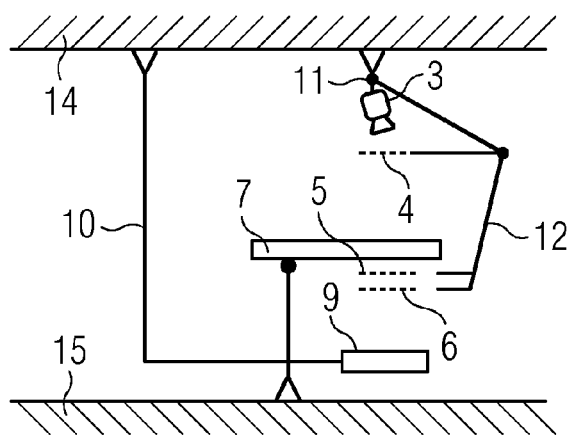
FIG. 2 depicts one embodiment of a slot scanning device with two ceiling stands.
Figure 3:
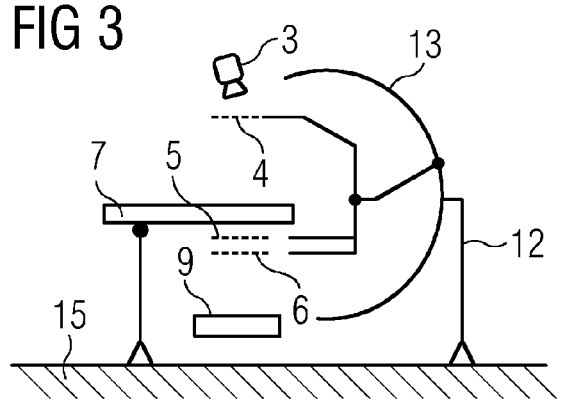
FIG. 3 depicts one embodiment of a slot scanning device with a C-arm.

FIGS. 1-3 depict schematic examples of slot scanning devices for x-ray phase contrast imaging, including an x-ray emitter 3, an x-ray detector 9, a patient couch 7 and a grating arrangement. The grating arrangement has a first x-ray grating 4, a second x-ray grating 5, and a third x-ray grating 6. The second and third x-ray gratings 5 and 6 are situated under the couch board (e.g., tabletop) of the patient couch 7 in front of the x-ray detector 9. The patient couch 7 serves to mount an object (not depicted) that is irradiated by the x-ray beam fan of the x-ray emitter 3. The object (e.g., a patient) is displaceable together with the patient couch 7.

In FIGS. 1 and 2, the x-ray detector 9 is fastened to a first ceiling stand 10 and may be displaced with the aid of the first ceiling stand 10 arranged at the ceiling 14. In FIG. 1, the x-ray emitter 3 is connected to a second ceiling stand 11 and may be displaced therewith. The second ceiling stand 11 is arranged at the ceiling 14. In the arrangement according to FIG. 1, the three x-ray gratings 4, 5, and 6 are connected to a floor stand 12. The floor stand 12 stands on the floor 15. The x-ray gratings 4, 5 and 6 may likewise be moved.

In the arrangement according to FIG. 2, the x-ray emitter 3 and the three x-ray gratings 4, 5 and 6 are fastened together to the second ceiling stand 11 and may be displaced therewith. The x-ray emitter 3, the x-ray detector 9 and the three x-ray gratings 4, 5 and 6 are movably arranged at a C-arm 13 in the arrangement according to FIG. 3. The C-arm 13 is arranged on the floor 15 with the floor stand 12.

In all exemplary embodiments in accordance with FIGS. 1-3, position marker elements (not depicted) are attached to one of the x-ray gratings 4, 5 or 6 and the patient couch 7. The position marker elements are irradiated by the x-ray beam fan of the x-ray emitter 3 and are visible in the x-ray images registered by the x-ray detector 9 (e.g., in an absorption image, a dark-field image, and/or a phase contrast image). With the aid of image processing software, the distances of the position marker elements from one another may be determined. As a result, there may be an exact registration of the relative location of the object on the patient couch 7 in relation to the x-ray gratings 4, 5 and 6 (e.g., in relation to the x-ray beam fan). Mechanical measuring aids for determining the position may thus be dispensed with. Consequently, the position marker elements serve as adjustment aids. An accuracy of less than 0.1 mm may be obtained with the aid of these devices. All components of the slot scanning device may be moved relative to one another. By way of example, the x-ray detector 9 (e.g., in the case of an arrangement without a stray radiation grid in front of the x-ray detector 9) may be displaced together with the patient couch 7 when recording the x-ray image, with the x-ray emitter 3 and the three x-ray gratings 4, 5 and 6 being stationary.

Figure 4:
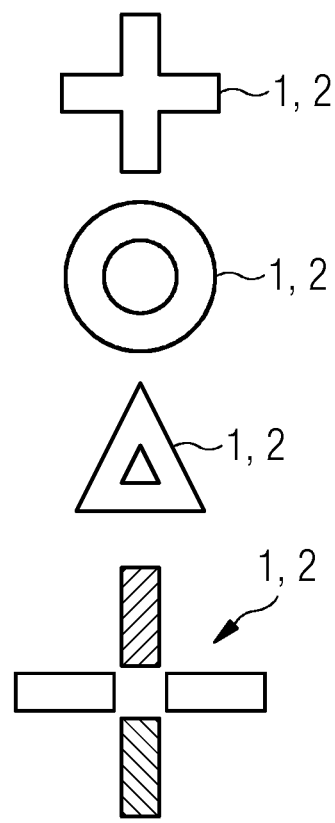
FIG. 4 depicts examples of position marker elements.

FIG. 4 depicts exemplary embodiments of the first and the second position marker elements 1 and 2. In principle, all plane geometric forms may be used. A cross, a circular ring, a triangle with a triangular cutout, and a cross with a central gap lend themselves to simple automated image evaluation. The position marker elements 1 and 2 have a thickness of approximately 10 to 500 μm and a maximum extent (diameter) of between approximately 150 μm and 25 mm. The web width of the position marker elements 1 and 2 is approximately 30 to 500 μm in the case of an assumed detector pixel dimension of 50 to 140 μm.

A metal layer may be used for absorption signals, a powdered lime layer may be used for dark-field signals, and a plexiglass layer may be used for phase signals. All signal forms may be combined with one another, as indicated in the cross with the central gap. For example, two of the four arms of the cross are embodied for absorption, one arm of the cross is embodied for the phase signal, and one arm of the cross is embodied for the dark-field signal.

Figure 5:
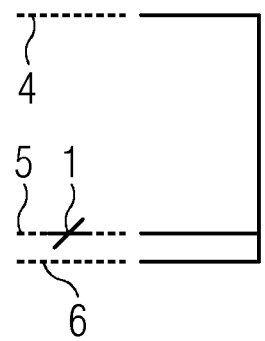
FIG. 5 depicts one embodiment of a position marker element on an x-ray grating.

FIG. 5 schematically depicts a grating arrangement with the three x-ray gratings 4, 5 and 6 according to one of FIG. 1 to FIG. 3. The first position marker element 1 is provided on the periphery of the second x-ray grating 5. In one embodiment, the first position marker element 1 lies on the edge of the used beam path. The first position marker element 1 may alternatively also be arranged on the third x-ray grating 6.

Figure 6:
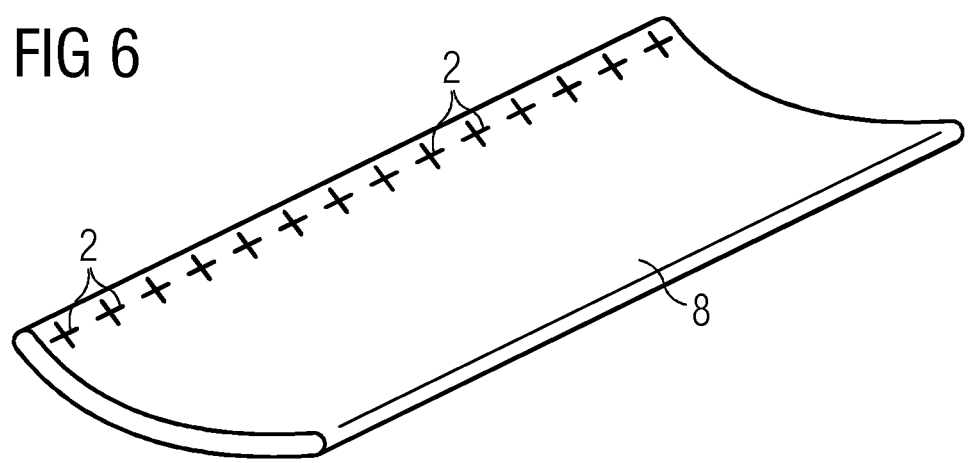
FIG. 6 depicts one embodiment of a position marker element on a couch board of a patient couch.

FIG. 6 depicts the couch board 8 of a patient couch 7 for an arrangement according to one of FIG. 1 to FIG. 3. The second position marker elements 2 are arranged peripherally on the couch board 8 in the longitudinal direction of the couch board 8. Between one another, the second position marker elements 2 have a gap of between 1 and 10 cm. For example, at least one second position marker element 2 may always come to rest in the region irradiated during the slot scanning method.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A device for slot scanning phase contrast x-ray imaging, the device comprising:
    an x-ray emitter;
    a plurality of x-ray gratings;
    a patient couch;
    an x-ray detector;
    a plurality of position marker elements arranged in a beam path of the x-ray emitter, the plurality of position marker elements being configured and arranged to be visible in an x-ray image, wherein a first position marker element is arranged on one x-ray grating of the plurality of x-ray gratings and a second position marker element is arranged on the patient couch; and
    an image processing unit configured to register a relative position of an object on the patient couch in relation to an x-ray beam fan of the x-ray emitter based on a location and a distance of the plurality of position marker elements from one another in the x-ray image.

2. The device of claim 1, wherein the plurality of position marker elements comprises a plurality of second position marker elements, the plurality of second position marker elements comprising the second marker element, and
    wherein the plurality of second position marker elements are arranged on a surface of a couch board of the patient couch in a longitudinal direction of the couch board.

3. The device of claim 1, wherein the image processing unit is configured to establish the location and the distance of the plurality of position marker elements from one another.

4. The device of claim 1, wherein each position marker element of the plurality of position marker elements is configured as a cross, a circular ring or a triangle.

5. The device of claim 1, wherein the plurality of position marker elements include regions that are visible in a dark-field image, a phase contrast image, an absorption image, or any combination thereof.

6. The device of claim 1, wherein each position marker element of the plurality of position marker elements has a layer thickness of 10 µm to 500 µm and a diameter of 150 µm to 25 mm.

7. The device of claim 2, wherein the image processing unit is configured to establish the location and the distance of the plurality of position marker elements from one another.

8. The device of claim 2, wherein each position marker element of the plurality of position marker elements is configured as a cross, a circular ring or a triangle.

9. The device of claim 2, wherein the plurality of position marker elements include regions that are visible in a dark-field image, a phase contrast image, an absorption image, or any combination thereof.

10. The device of claim 2, wherein each position marker element of the plurality of position marker elements has a layer thickness of 10 µm to 500 µm and a diameter of 150 µm to 25 mm.

11. A method for slot-scanning phase contrast x-ray imaging, the method comprising:
    establishing, by an image processing unit with the aid of position marker elements visible in an x-ray image and are arranged in a beam path of an x-ray emitter, a relative position of an object to be irradiated in relation to an x-ray beam fan of the x-ray emitter based on a location and a distance of the position marker elements from one another in the x-ray image,
    wherein a first position marker element is arranged on an x-ray grating and a second position marker element is arranged on a patient couch supporting the object.

12. The method of claim 11, wherein image processing software is used to establish the location and the distance of the first position marker element from the second position marker element.

* * * * *